(12) United States Patent
Spino et al.

(10) Patent No.: US 8,703,156 B2
(45) Date of Patent: Apr. 22, 2014

(54) LIQUID FORMULATION FOR DEFERIPRONE WITH PALATABLE TASTE

(75) Inventors: Michael Spino, Pickering (CA); Anita Hui, Unionville (CA); Cihua Yang, Richmond Hill (CA); Mohammed N. Kabir, Richmond Hill (CA)

(73) Assignee: Apotex Technologies Inc., Toronto, Ontario (CA)

(*) Notice: Subject to any disclaimer, the term of this patent is extended or adjusted under 35 U.S.C. 154(b) by 549 days.

(21) Appl. No.: 12/989,127

(22) PCT Filed: Apr. 25, 2008

(86) PCT No.: PCT/CA2008/000784
§ 371 (c)(1),
(2), (4) Date: Oct. 22, 2010

(87) PCT Pub. No.: WO2009/129592
PCT Pub. Date: Oct. 29, 2009

(65) Prior Publication Data
US 2011/0039897 A1    Feb. 17, 2011

(51) Int. Cl.
*A61K 31/724* (2006.01)
*A61K 31/137* (2006.01)

(52) U.S. Cl.
USPC .............................. 424/400; 514/58; 514/312

(58) Field of Classification Search
USPC .............................................. 424/400; 514/58
See application file for complete search history.

(56) References Cited

U.S. PATENT DOCUMENTS

| | | |
|---|---|---|
| 2,918,402 A | 12/1959 | Frederick |
| RE25,831 E | 8/1965 | Moore |
| 4,585,780 A | 4/1986 | Hider et al. |
| 5,154,926 A | 10/1992 | Kawasaki et al. |
| RE34,313 E | 7/1993 | Hider et al. |
| 5,616,621 A | 4/1997 | Popli et al. |
| 5,658,919 A | 8/1997 | Ratnaraj et al. |
| 5,730,997 A | 3/1998 | Lienhop et al. |
| 5,763,449 A | 6/1998 | Anaebonam et al. |
| 5,928,885 A | 7/1999 | Nixon et al. |
| 5,962,461 A | 10/1999 | Anaebonam et al. |
| 6,133,322 A | 10/2000 | Rustin et al. |
| 6,472,378 B2 | 10/2002 | von Borstel |
| 6,506,911 B2 | 1/2003 | Hider et al. |
| 6,806,256 B2 | 10/2004 | Ulrich et al. |
| 6,855,711 B1 | 2/2005 | Warshawsky et al. |
| 6,906,052 B2 | 6/2005 | Shah |
| 6,956,028 B2 | 10/2005 | von Borstel |
| 6,989,397 B1 | 1/2006 | Richardson et al. |
| 2002/0068758 A1 | 6/2002 | Hider et al. |
| 2003/0158234 A1 | 8/2003 | Spino et al. |
| 2003/0187019 A1* | 10/2003 | Ullah et al. .................. 514/312 |
| 2004/0101521 A1 | 5/2004 | Andersen |
| 2004/0116401 A1 | 6/2004 | Shah |
| 2005/0250738 A1* | 11/2005 | Mosher et al. ................. 514/58 |
| 2006/0030619 A1 | 2/2006 | Liu et al. |
| 2006/0093630 A1 | 5/2006 | Buehler |
| 2006/0100189 A1 | 5/2006 | Gurtner et al. |
| 2006/0234927 A1 | 10/2006 | Youdim et al. |
| 2006/0281748 A1 | 12/2006 | Gurtner et al. |
| 2007/0197469 A1 | 8/2007 | Murthy |
| 2008/0242706 A1 | 10/2008 | Tam et al. |
| 2009/0023784 A1 | 1/2009 | Munnich |

FOREIGN PATENT DOCUMENTS

| | | |
|---|---|---|
| CA | 1095921 A1 | 2/1981 |
| CA | 1290096 C | 10/1991 |
| CA | 2100158 A1 | 7/1992 |
| CA | 2226340 A1 | 1/1997 |
| CA | 2287907 A1 | 12/1998 |
| CA | 1340608 C | 6/1999 |
| DE | 10336497 A1 | 3/2005 |
| EP | 0120670 A1 | 10/1984 |
| EP | 0138420 A2 | 4/1985 |
| EP | 0336369 A1 | 10/1989 |
| EP | 1025858 A1 | 8/2000 |
| GB | 2136807 A | 9/1984 |
| WO | 9520584 A1 | 8/1995 |
| WO | 9527485 A1 | 10/1995 |
| WO | 0117530 A1 | 3/2001 |
| WO | 0202114 A1 | 1/2002 |
| WO | 03075910 A1 | 9/2003 |
| WO | 2007095728 A1 | 8/2007 |
| WO | 2008116301 A1 | 10/2008 |
| WO | 2009103950 A1 | 9/2009 |

OTHER PUBLICATIONS

Clinical trial No. NCT00529152, Sep. 12, 2007, U.S. FDA REsources.*
Apotex, Title: Ferriprox 100 mg/mL oral solution, Aug. 25, 1999, drugs.com/UK.*
International search report of PCT/CA2008/000784, Title: Ferriprox—Procedural steps taken and scientific information after the authorization changes made, Jan. 6, 2004.*
Olivieri et al., Title: Iorn-Chelation Therapy with Oral Deferiprone in Patients with Thalassemia Major, N. Engl. J. Med.; published Apr. 6, 1995.*
Akers, Michael J. "Parenteral Preparations", Remington: The Science and Practice of Pharmacy, Ed. David B. Troy, 2006, pp. 802-836, Lippincott Williams & Wilkins, Baltimore.
Block, Lawrence H. "Medicated Topicals", Remington: The Science and Practice of Pharmacy, Ed. David B. Troy, 2006, pp. 871-888, Lippincott Williams & Wilkins, Baltimore.

(Continued)

*Primary Examiner* — Richard Schnizer
*Assistant Examiner* — Yanzhi Zhang
(74) *Attorney, Agent, or Firm* — The Webb Law Firm

(57) ABSTRACT

An oral pharmaceutical liquid formulation comprising deferiprone and a taste masking composition, said taste masking composition comprising an effective amount of a sweetener (such as sucralose) per liter of liquid composition, an effective amount of a thickening and suspension aid, (for example hydroxyethylcellulose), per liter of liquid composition, an effective amount of a humectant (such as glycerin) per liter of liquid composition, and an effective amount of at least one flavoring agent, wherein a final form of said taste-masked pharmaceutical has a substantially non-bitter and palatable taste.

17 Claims, No Drawings

(56) References Cited

OTHER PUBLICATIONS

Crowley, Michael M. "Solutions, Emulsions, Suspensions, and Extracts", Remington: The Science and Practice of Pharmacy, Ed. David B. Troy, 2006, pp. 745-775, Lippincott Williams & Wilkins, Baltimore.

Ding, Xuan et al. "Extended-Release and Targeted Drug Delivery Systems", Remington: The Science and Practice of Pharmacy, Ed. David B. Troy, 2006, pp. 939-964, Lippincott Williams & Wilkins, Baltimore.

Lang, John C. et al. "Opthalmic Preparations", Remington: The Science and Practice of Pharmacy, Ed. David B. Troy, 2006, pp. 850-870, Lippincott Williams & Wilkins, Baltimore.

O'Connor, Robert E. et al. "Powders", Remington: The Science and Practice of Pharmacy. Ed. David B. Troy, 2006, pp. 702-719, Lippincott Williams & Wilkins, Baltimore.

Porter, Stuart C. "Coating of Pharmaceutical Dosage Forms," Remington: The Science and Practice of Pharmacy, Ed. David B. Troy, 2006, pp. 929-938, Lippincott Williams & Wilkins, Baltimore.

Rudnic, Edward M. et al. "Oral Solid Dosage Forms", Remington: The Science and Practice of Pharmacy, Ed. David B. Troy, 2006, pp. 889-928, Lippincott Williams & Wilkins, Baltimore.

Schlindwein, Walkiria et al. "New lipophilic 3-hydroxy-4-pyridinonate iron(III) complexes: synthesis and EXAFS structural characterisation", Dalton Transactions, 2006, pp. 1313-1321.

Sciarra, John C. et al. "Aerosols", Remington: The Science and Practice of Pharmacy, Ed. David B. Troy, 2006, pp. 1000-1017, Lippincott Williams & Wilkins, Baltimore.

Turco, Salvatore J. "Intravenous Admixtures", Remington: The Science and Practice of Pharmacy. Ed. David B. Troy, 2006, pp. 837-849, Lippincott Williams & Wilkins, Baltimore.

Avramovich-Tirosh, Yael et al. "Therapeutic targets and potential of the novel brain-permeable multifunctional iron chelator-monomine oxidase inhibitor drug, M-30, for the treatment of Alzheimer's disease", Journal of Neurochemistry, 2007, pp. 490-502, vol. 100.

Barnham, Kevin J. et al., "Metal-Protein Attenuating Compounds (MPACs) for the Treatment of Alzheimer's Disease", Drug Design Reviews—Online, 2004, pp. 75-82, vol. 1.

Bush, Ashley I. et al. "Rapid Induction of Alzheimer A# Amyloid Formation by Zinc", Science, 1994, pp. 1464-1467, vol. 265, No. 5177.

Cherny, Robert A. et al., "Aqueous Dissolution of Alzheimer's Disease Aβ Amyloid Deposits by Biometal Depletion", The Journal of Biological Chemistry, 1999, pp. 23223-23228. vol. 274, No. 33.

Escudar-Gilabert, L. et al., "Potential of biopartitioning micellar chromatography as an in vitro technique for predicting drug penetration across the blood-brain barrier", Journal of Chromatography B, 2004, pp. 193-201, vol. 807.

Gabbita, S. Prasad et al., "Increased Nuclear DNA Oxidation in the Brain in Alzheimer's Disease", Journal of Neurochemistry, 1998, pp. 2034-2040, vol. 71, No. 5.

Gaeta, Alessandra et al. "The crucial role of metal ions in neurodegeneration: the basis for a promising therapeutic strategy", British Journal of Pharmacology, 2005, pp. 1041-1059, vol. 146.

Kontoghiorghes, G.J. et al. "The Design and Development of Deferiprone (L1) and Other Iron Chelators for Clinical Use: Targeting Methods and Application Prospects", Current Medicinal Chemistry, 2004, pp. 2161-2183, vol. 11.

Lovell, M.A. et al. "Copper, iron and zinc in Alzheimer's disease senile plaques", Journal of the Neurological Sciences, 1998, pp. 47-52, vol. 158.

Pardridge, William M., "CNS Drug Design Based on Principles of Blood-Brain Barrier Transport", Journal of Neurochemistry, 1998, pp. 1781-1792, vol. 70, No. 5.

Ritchie, Craig W. et al. "Metal-Protein Attenuation With Iodochlorhydroxyquin (Clioquinol) Targeting Aβ Amyloid Deposition and Toxicity in Alzheimer Disease—A Pilot Phase 2 Clinical Trial", Arch Neurol, 2003, pp. 1685-1691, vol. 60.

Sayre, Lawrence M. et al. "In Situ Oxidative Catalysis by Neurofibrillary Tangles and Senile Plaques in Alzheimer's.Disease: A Central Role for Bound Transition Metals", Journal of Neurochemistry, 2000, pp. 270-279. vol. 74, No. 1.

Usansky, Helen H. et al. "Computation of Log BB values for compounds transported through carrier-mediated mechanisms using in vitro permeability data from brain microvessel endothelial cell (BMEC) monolayers", Pharmaceutical Research, 2003, p. 390, vol. 20, Issue 3.

Becker, Erika et al. "Frataxin: its role in iron metabolism and the pathogenesis of Friedreich's ataxia", The International Journal of Biochemistry & Cell Biology, 2001, pp. 1-10, vol. 33.

Boddaert, Nathalie et al. "Selective Iron Chelation in Friedreich Ataxia. Biological and Clinical Implications", Blood, 2007, pp. 401-408, vol. 110.

Breuer, William et al. "Desferrioxamine-chelatable iron, a component of serum non-transferrin-bound iron, used for assessing chelation therapy", Blood, 2001, pp. 792-798, vol. 97, No. 3.

Campuzano, Victoria et al. "Friedreich's Ataxia: Autosomal Recessive Disease Caused by an Intronic GAA Triplet Repeat Expansion", Science, 1996, vol. 271.

Cano, Stefan J. et al., "International Cooperative Ataxia Rating Scale (ICARS): Appropriate for Studies of Friedreich's Ataxia?", Movement Disorders, 2005, pp. 1585-1591, vol. 20., No. 12.

Chamberlain, Susan et al., "Mapping of mutation causing Friedreich's ataxia to human chromosome 9", Nature, 1988, pp. 248-250, vol. 334.

Chantrel-Groussard, Karine et al., "Disabled early recruitment of antioxidant defenses in Friedreich's ataxia", Human Molecular Genetics, 2001, pp. 2061-2067, vol. 10, No. 19.

Delatycki, Martin B. et al. "Direct Evidence that Mitochondrial Iron Accumulation Occurs in Friedreich Ataxia", Annals of Neurology, 1999, pp. 673-675, vol. 45, No. 5.

Delatycki, Martin B. et al. "Friedreich ataxia: from genes to therapies?", Medical Journal of Australia, 2005, p. 439, vol. 182. No. 9.

Gakh, Oleksandr et al. "Mitochondrial iron detoxification is a primary function of frataxin that limits oxidative damage and preserves cell longevity", Human Molecular Genetics, 2006, pp. 467-479, vol. 15, No. 3.

Glickstein, Hava et al. "Intracellular labile iron pools as direct targets of iron chelators: a fluorescence study of chelator action in living cells", Blood, 2005, pp. 3242-3250, vol. 106, No. 9.

Goncalves, Sergio et al. "Deferiprone targets aconitase: Implication for Friedreich's ataxia treatment", BMC Neurology, 2008, vol. 8, No. 20.

Haacke, E. Mark et al. "Imaging iron stores in the brain using magnetic resonance imaging", Magnetic Resonance Imaging, 2005, pp. 1-25, vol. 23.

Hausse, A. O. et al. "Idebenone and reduced cardiac hypertrophy in Friedreich's ataxia", Heart, 2002, pp. 346-349, vol. 87.

Hershko, Chaim et al. "Iron overload and chelation", Hematology, 2005, pp. 171-173, vol. 10, Supplement 1.

Lim, C.K. et al. "Protection against Hydrogen Peroxide-Mediated Cytotoxicity in Friedreich's Ataxia Fibroblasts using Novel Iron Chelators of the 2-Pyridylcarboxaldehyde Isonicotinoyl Hydrazone Class", Molecular Pharmacology, 2008, pp. 225-235, vol. 74., No. 1.

Lodi, Raffaele et al. "Mitochondrial Dysfunction in Friedreich's Ataxia", Biological Signals and Receptors, 2001, pp. 263-270, vol. 10.

Lovejoy, David B. et al. "PCTH: A Novel Orally Active Chelator for the Treatment of Iron Overload Disease", Hemoglobin, 2006, pp. 93-104, vol. 30, No. 1.

Mandel, Silvia A. et al., "Multifunctional Activities of Green Tea Catechins in Neuroprotection", Neuro-Signals, 2005, pp. 46-60, vol. 14.

Molina-Holgado, Francisco et al. "Neuroprotective Actions of an Iron Chelator Against Alzheimer's Disease-Relevant Insults", Alzheimer's and Dementia, 2006, p. S631, vol. 2, Issue 3.

Olivieri, Nancy F. et al. "Iron-Chelation Therapy with Oral Deferiprone in Patients with Thalassemia Major", The New England Journal of Medicine, 1995, pp. 918-922, vol. 332, No. 14.

Olivieri, Nancy F. et al. "Long-Term Safety and Effectiveness of Iron-Chelation Therapy with Deferiprone for Thalassemia Major", The New England Journal of Medicine, pp. 417-423, vol. 339, No. 7.

(56) References Cited

OTHER PUBLICATIONS

Pearce, J.M. "Friedreich's ataxia", Journal of neurology neurosurgery and psychiatry, 2004, p. 688, vol. 75, No. 5.
Pennell, Dudley J. et al. "Randomized controlled trial of deferiprone or deferoxamine in beta-thalassemia major patients with asymptomatic myocardial siderosis", Blood, 2006, pp. 3738-3744, vol. 107, No. 9.
Pootrakul, Pensri et al. "Labile plasma iron (LPI) as an indicator of chelatable plasma redox activity in iron-overloaded β-thalassemia/ HbE patients treated with an oral chelator", Blood, 2004, pp. 1504-1510, vol. 104, No. 5.
Crivori, P. et al., "Predicting Blood-Brain Barrier Permeation from Three-Dimensional Molecular Structure", Journal of Medicinal Chemistry, 2000, pp. 2204-2216, vol. 43.
Berkovitch et al. "The Efficacy of Oral Deferiprone in Acute Iron Poisoning". American Journal of Emergency Medicine. Jan. 2000. pp. 36-40. vol. 18. No. 1.
Giardina et al. "Chelation Therapy in β-Thalassemia: An Optimistic Update". Seminars in Hematology. Oct. 2001. pp. 360-366. vol. 38, No. 4.
Tam et al. "Iron Chelator Research: Past, Present, and Future". Current Medicinal Chemistry. 2003. pp. 983-995. vol. 10, No. 12.
"Ferriprox—Procedurual steps taken and scientific information after the authorisation changes made after Jan. 6, 2004". http:/www.emea.europa.eu/humandocs/PDFs/EPAR/Ferriprox/038799en8b.pdf on Nov. 12, 2008. on Nov. 12, 2008.
"Annex I—Summary of Product Characteristics" http://www.ferriprox.com/aboutferriprox/SPC_solution.pdf. on Nov. 12, 2008.
European Commission Decision of Aug. 25, 1999 (labeled "Not for Publication") approving Apotex's Ferriprox® tablets, available at http://ec.europa.eu/health/documents/community-register/html/h108.htm (Jul. 17, 2013).
European Commission Decision of Nov. 19, 2007 (labeled "Not for Publication") approving Apotex's Ferriprox® 100mg/ml oral solution, available at http://ec.europa.eu/health/documents/community-register/html/h108.htm (Jul. 17, 2013).
Annex I, "Summary of Product Characteristics", to European Commission Decision of Nov. 19, 2007 (labeled "Not for Publication") approving Apotex's Ferriprox® 100mg/ml oral solution, available at http://ec.europa.eu/health/documents/community-register/html/h108.htm (Jul. 17, 2013).
"Summary of Community Decisions on Marketing Authorizations in Respect of Medicinal Products from Nov. 1, 2007 to Nov. 30, 2007," Official Journal of the European Union C316/42 (Dec. 28, 2007), http://ec.europa.eu/health/documents/community-register/html/h108.htm.
Porter, John B., "A Risk-Benefit Assessment of Iron-Chelation Therapy", Drug Safety,1997, pp. 407-421, vol. 17., No. 6.
Richardson, Des R. "The therapeutic potential of iron chelators", Expert Opinion on Investigational Drugs, 1999, pp. 2141-2158, vol. 8. No. 12.
Richardson, D.R. et al. "Development of potential iron chelators for the treatment of Friedreich's ataxia: ligands that mobilize mitochondrial iron", Biochemica et Biophysica Acta, 2001, pp. 133-140, vol. 1536.
Richardson, D.R., "Friedrich's ataxia: iron chelators that target the mitochondrion as a therapeutic strategy?", Expert Opinion on Investigational Drugs, 2003, pp. 235-245, vol. 12, No. 2.
Richardson, Des R. "The controversial role of deferiprone in the treatment of thalassemia", Journal of Laboratory and Clinical Medicine, 2001, pp. 324-329, vol. 137, No. 5.
Richardson, Des R., "Novel chelators for Central Nervous System Disorders That Involve Alterations in the Metabolism of Iron and Other Metal Ions", Annals of the New York Academy of Sciences, 2004, pp. 326-341, vol. 1012.
Rötig, Agnès et al., Aconitase and mitochondrial iron-sulphur protein deficiency in Friedreich ataxia, Nature Genetics, 1997, pp. 215-217, vol. 17.
Rund, Deborah et al., "β-Thalassemia", The New England Journal of Medicine, 2005, pp. 1135-1146, vol. 353. No. 11.
Rustin, Pierre et al., "Effect of idebenone on cardiomyopathy in Friedreich's ataxia: a preliminary study", The Lancet, 1999, pp. 477-479, vol. 354.
Shvartsman, Maya et al., "Non-transferrin-bound iron reaches mitochondria by a chelator-inaccessible mechanism: biological and clinical implications", American Journal of Physiology—Cell Physiology, 2007, pp. 1383-1394, vol. 293.
Simon, Delphine et al., "Friedreich Ataxia Mouse Models with Progressive Cerebellar and Sensory Ataxia Reveal Autophagic Neurodegeneration in Dorsal Root Ganglia", The Journal of Neuroscience, 2004, pp. 1987-1995, vol. 24. No. 8.
Sturm, Brigitte et al., "Friedreich's Ataxia, No Changes in Mitochondrial Labile Iron in Human Lymphoblasts and Fibroblasts—A Decrease in Antioxidative Capacityr?", The Journal of Biological Chemistry, 2009, pp. 6701-6706, vol. 280, No. 8.
Voncken, Max et al., "Friedreich ataxia—update on pathogenesis and possible therapies", Neurogenetics, 2004, pp. 1-8, vol. 5.
Waldvogel, Daniel et al., "Increased Iron in the Dentate Nucleus of Patients with Friedreich's Ataxia", Annals of Neurology, 1999, pp. 123-125, vol. 46, No. 1.
Whitnall, Megan et al., "The MCK mouse heart model of Friedreich's ataxia: Alterations in iron-regulated proteins and cardiac hypertrophy are limited by iron chelation", PNAS, 2008, pp. 9757-9762, vol. 105, No. 28.
Whitnall, Megan et al., "Iron: A new Target for Pharmacological Intervention in Neurodegenerative Diseases", Seminars in Pediatric Neurology, 2006, pp. 186-197, vol. 13.
Sohn, Yang-Sung et al., "Redistribution of accumulated cell iron, A modality of chelation with therapeutic implications", Blood First Edition Paper, prepublished online Nov. 1, 2007.
Wilson, Robert B. et al., "Normal Serum Iron and Ferritin Concentrations in Patients with Friedreich's Ataxia", Annals of Neurology, 1998, pp. 132-134, vol. 44, No. 1.
Forni, Gian Luca et al., "Regression of symptoms after selective iron chelation therapy in a case of neurodegeneration with brain iron accumulation.", Mov Discord, 2008, pp. 904-907, vol. 23, No. 6.
Franchini, Massimo et al. "Iron-chelation therapy: an update", The Hematology Journal, 2004, pp. 287-292, vol. 5.
Delatycki, Martin B. et al. "Friedreich ataxia: an overview", Journal of Medical Genetics, 2000, pp. 1-8, vol. 37.
Hershko, Chaim et al. "Objectives and Mechanism of Iron Chelation Therapy", Annals of the New York Academy of Science, 2005, pp. 124-135, vol. 1054.
Hershko, Chaim et al. "ICL670A: a new synthetic oral chelator: evaluation in hypertransfused rats with selective radioiron probes of hepatocellular and reticuloendothelial iron stores and in iron-loaded rat heart cells in culture", Blood, 2001, pp. 1115-1122, vol. 97.
Lodi, R. et al. "Antioxidant Treatment Improves in Vivo Cardiac and Skeletal Muscle Bioenergetics in Patients with Friedreich's Ataxia", Annals of Neurology, May 2001, pp. 590-596, vol. 49, No. 5.
Avis, Kenneth E., et al., "Parenteral Preparations", Remington: The Science and Practice of Pharmacy, Ed. Daniel Limmer, 2000, pp. 780-806, Lippincott Williams & Wilkins, Baltimore.
Block, Lawrence H., "Medicated Topicals", Remington: The Science and Practice of Pharmacy, Ed. Daniel Limmer, 2000, pp. 836-857, Lippincott Williams & Wilkins, Baltimore.
Hecht, Gerald, "Opthalmic Preparations", Remington: The Science and Practice of Pharmacy, Ed. Daniel Limmer, 2000, pp. 821-835, Lippincott Williams & Wilkins, Baltimore.
Lee, Thomas Wai-Yip et al., "Controlled-Release Drug-Delivery Systems", Remington: The Science and Practice of Pharmacy, Ed. Daniel Limmer, 2000, pp. 903-929, Lippincott Williams & Wilkins, Baltimore.
Nairn, J.G., "Solutions, Emulsions, Suspensions, and Extracts", Remington: The Science and Practice of Pharmacy, Ed. Daniel Limmer, 2000, pp. 721-752, Lippincott Williams & Wilkins, Baltimore.
Porter, Stuart C., "Coating of Pharmaceutical Dosage Forms," Remington: The Science and Practice of Pharmacy, Ed. Daniel Limmer, 2000, pp. 894-902, Lippincott Williams & Wilkins, Baltimore.
Rudnic, Edward M. et al., "Oral Solid Dosage Forms",Remington: The Science and Practice of Pharmacy, Ed. Daniel Limmer, 2000, pp. 858-893, Lippincott Williams & Wilkins, Baltimore.

(56) References Cited

OTHER PUBLICATIONS

Sciarra, John J. et al., "Aerosols", Remington: The Science and Practice of Pharmacy, Ed. Daniel Limmer, 2000, pp. 963-979, Lippincott Williams & Wilkins, Baltimore.

Turco, Salvatore J., "Intravenous Admixtures", Remington: The Science and Practice of Pharmacy. Ed. Daniel Limmer, 2000, pp. 807-820, Lippincott Williams & Wilkins, Baltimore.

Buss, Joan L. et al., "The Role of Iron Chelation in Cancer Therapy", Current Medicinal Chemistry, 2003, pp. 1021-1034, vol. 10.

Carmichael, James et al., "Evaluation of a Tetrazolium-based Semiautomated Colorimetric Assay: Assessment of Chemosensitivity Testing", Cancer Research, Feb. 15, 1987, pp. 936-942, vol. 47.

Cooper, Mindy A. et al., "Urinary Iron Speciation in Nephrotic Syndrome", American Journal of Kidney Diseases, Feb. 1995, pp. 314-319, vol. 25, No. 2.

Crumbliss, Alvin L., "Iron Chelation in Biology", Virtual Free Radical School, http://www.medicine.uiowa.edu/FRRB/VirtualSchool/Crumbliss-Fe.pdf. published online, 2002.

Dhungana, Suraj et al., "Fe(III) Coordination Properties of a New Saccharide-Based Exocyclic Trihydroxamate Analogue of Ferrichrome", Inorganic Chemistry, 2003, pp. 42-50, vol. 42.

Dean, Roger T. et al., "The Action of Nine Chelators on Iron-Dependent Radical Damage", Free Radical Res., 1994, pp. 83-101, vol. 20, No. 2.

Gutteridge, John M.C., "Superoxide-Dependent Formation of Hydroxyl Radicals from Ferric-Complexes and Hydrogen Peroxide: An Evaluation of Fourteen Iron Chelators", Free Radical Res., 1990, pp. 119-125, vol. 9, No. 2.

Dehkordi, Lotfollah S., "Basic 3-hydroxypyridin-4-ones: Potential antimalarial agents", European Journal of Medicinal Chemistry, 2008, pp. 1035-1047, vol. 43.

Molina-Holgado, Francisco et al., "Metals ions and neurodegeneration", Biometals, 2007, pp. 639-654, vol. 20.

Kang, Sam Sik et al., "Neuroprotective effects of flavones on hydrogen peroxide-induced apoptosis in SH-SY5Y neuroblastoma cells", Bioorganic & Medicinal Chemistry Letters, 2004, pp. 2261-2264, vol. 14.

Kerns, E. et al., "Blood-Brain Barrier", Drug-Like Properties: Concepts, Structure Design and Methods, 2008, Elsevier.

Kurz, Tino et al., "Relocalized redox-active lysosomal iron is an important mediator of oxidative-stress-induced DNA damage", Biochemical Journal, 2004, pp. 1039-1045, vol. 378.

Manitpisitkul, Prasarn et al., "Whatever happened to casssette-dosing pharmacokinetics?", Drug Discovery Today, Aug. 2004, pp. 652-658, vol. 9, No. 15.

Mosmann, Tim, "Rapid Colorimetric Assay for Cellular Growth and Survival: Application to Proliferation and Cytotoxicity Assays", Journal of Immunological Methods, 1983, pp. 55-63, vol. 65.

Liu, Zu D. et al., "Design, Synthesis and Evaluation of N-Basic Substituted 3-Hydroxypyridin-4-ones: Orally Active Iron Chelators with Lysosomotrophic Potential", Journal of Pharmacy and Pharmacology, 2000, pp. 263-272, vol. 52.

Pierre, J.L. et al., "Iron and activated oxygen species in biology: The basic chemistry", BioMetals, 1999, pp. 195-199, vol. 12.

Persson, H. Lennart et al., "Iron-binding drugs targeted to lysosomes: a potential strategy to treat inflammatory lung disorders", Expert Opinion on Investigational Drugs, 2005, pp. 997-1008, vol. 14, No. 8.

Sopher, Bryce L. et al., "Cytotoxicity mediated by conditional expression of a carboxyl-terminal derivative of the β-amyloid precursor protein", Molecular Brain Research, 1994, pp. 207-217, vol. 26.

Friedreich, N., Virchow's Arch Path Anat, 1863, pp. 391-419, vol. 26.

File History for PCT WO 2007/085728, published as WO 2007/095728, published Aug. 30, 2007.

File History for U.S. Appl. No. 12/279,930, published as US 2009/0023784, published Jan. 22, 2009.

\* cited by examiner

US 8,703,156 B2

LIQUID FORMULATION FOR DEFERIPRONE WITH PALATABLE TASTE

FIELD OF THE INVENTION

The present invention relates to novel taste masked liquid deferiprone compositions for oral administration.

BACKGROUND OF THE INVENTION

Orally administered drugs are provided to the patient in many dosage forms, including solid forms such as capsules, caplets or tablets and liquid forms such as solutions, syrups, emulsions or suspensions. Pharmaceutically active agents administered in solid dosage form are usually intended to be swallowed whole. The disagreeable taste of the drug is generally not of concern when formulating oral solid dosage forms, because the pharmaceutical's taste can be easily masked with an exterior coating.

Children, older persons, and many other persons including disabled or incapacitated patients often have trouble swallowing tablets or capsules. In these situations, it is desirable to provide the drug either in a chewable solid form or a liquid form. For many patients, including pediatric and geriatric patients, a liquid oral dosage form is preferred over a chewable dosage form. A liquid dosage form is especially preferred for this class of patients because of the ease with which it may be swallowed. Additionally, patients may be more inclined to comply with their medication instruction if the dosages are easier to ingest, particularly for products administered in large doses, requiring several tablets at a time.

Some liquid pharmaceutical compositions formulated for use by pediatric or geriatric patients are often prepared by grinding a tablet dosage form into a powder and mixing the powder with a diluent. Such a formulation may cause some of the drug to remain undissolved, thereby affecting the therapeutic dose of drug in the composition. In addition, the powder exposes the unpleasant tasting pharmaceutically active agent, which may result in a lack of compliance due to the unacceptable taste. It is readily understood that such compositions are impractical and may result in underdosing or poor compliance.

A common formulation problem associated with liquid pharmaceutical dosage forms (such as solutions (including syrups or suspensions) is masking the disagreeable taste that a pharmaceutically active agent may often manifest when administered in a liquid dosage form. Many active ingredients, such as antibiotics, possess a strong, unpleasant and bitter taste. Deferiprone particularly has an extremely bitter taste as discussed in the Merck Index. Prior attempts to provide acceptable and palatable liquid deferiprone formulations have been unsuccessful.

Pfertec Limited of London England had previously prepared a liquid deferiprone formulation which was never approved, but was sold as a research drug only to physicians for use in patients on a named patient basis. The taste was unbearably unpleasant. There was no disclosure of the details of the Pfertec liquid deferiprone composition, but taste comparisons, conducted by the applicant, revealed they had failed to produce a palatable product for commercial purposes.

The prior art has shown extensive use of one or a combination of different flavoring methodologies to mask the bitter taste of drugs. For example, a flavor can be selected that complements the taste of the preparation, or a flavor with a longer intensity and stronger taste than the drug can be used. High levels of sweetening agents are often used to overwhelm bitterness with sweetness. The taste buds may also be anesthetized by menthol or mint flavors. These approaches are generally not very effective in masking the taste of a bitter drug, and a flavoring system that works with one drug often does not apply to another drug.

The prior art also indicates that taste masking may be achieved by increasing the viscosity of liquid preparations. Various combinations of viscosity modifiers for taste masking exist in the patent literature. For example, U.S. Pat. No. 5,616,621 provides alleged taste masked liquid preparations by increasing the viscosity with a combination of polyethylene glycol and sodium carboxymethylcellulose; and U.S. Pat. No. 5,658,919 discloses alleged taste masking of an acetaminophen suspension using a suspending system consisting of xanthan gum and a mixture of cellulosic polymers. The increase in viscosity is assumed to limit the contact of the drug with the tongue, presumably by slowing down salivary water uptake into the viscous liquid medicament, which can lead to dilution and dissolution of the taste-offending ingested medication. This approach is only moderately successful in reducing bitterness especially at high drug loading. While bitterness may be reduced at the onset, bitter aftertaste becomes prominent after swallowing because thick preparations are more difficult to wash down thus leaving behind some residual viscous liquid medicament in the mouth after swallowing. This bitter aftertaste is more prominent with water intake due to the reduction in viscosity and dilution of the residual liquid medicament and subsequent dissolution of the drug in the mouth.

Several other approaches have been pursued to address the unpleasant taste of a drug in a liquid format. U.S. Pat. No. 5,730,997 illustrates the use of a hyperosmotic liquid using a sugar derivative and maltose syrup for taste masking. U.S. Pat. No. 5,154,926 claims reduction of the bitter taste of acetaminophen syrup by using a water-soluble macromolecule with a polyhydric alcohol and/or polymer of a polyhydric alcohol of MW 300-400. U.S. Pat. Nos. 5,763,449 and 5,962,461 teach the use of a combination of povidone, C3-C6 polyol and ammonium glycyrrhizinate for taste masking. EP application No. 1025858A1 discloses relief of bitterness of basic drugs by combining propylene glycol with povidone and/or copolyvidone.

In the case of developing a palatable formulation for a liquid deferiprone product, several approaches were used without success, resulting in a product not much more palatable than the Pfertec product. Thus a series of iterative steps were taken to overcome the difficulty experienced in developing a liquid formulation for deferiprone that has a palatable taste.

It is therefore a primary aspect of the invention to provide a palatable liquid deferiprone formulation using a taste masking composition directed specifically at the offending taste generated by deferiprone.

It is yet another object of this invention to provide a taste masked liquid deferiprone formulation wherein the taste masking composition comprises a taste masking effective amount of sucralose and optionally at least one flavouring agent.

Further and other objects of the invention will become apparent to one skilled in the art when reviewing the following summary of the invention and the more detailed description of the preferred embodiments contained herein.

SUMMARY OF THE INVENTION

The present invention comprises a palatable liquid deferiprone formulation, essentially masking the very bitter and otherwise unpleasant tasting drug deferiprone.

The present invention provides for a novel flavored and taste-masked palatable deferirprone formulation. According to a primary aspect of the invention there is provided an oral pharmaceutical liquid formulation comprising deferiprone and a taste masking composition, said taste masking composition comprising an effective amount of a sweetener (such as sucralose) per liter of liquid composition, an effective amount of a thickening and suspension aid, (for example hydroxyethylcellulose), per liter of liquid composition, an effective amount of a humectant (such as glycerin) per liter of liquid composition, and an effective amount of at least one flavoring agent per liter of liquid composition, wherein a final form of said taste-masked pharmaceutical formulation has a substantially non-bitter palatable taste.

In another embodiment of the invention there is provided a taste masked palatable liquid deferiprone formulation wherein the taste masking formulation further comprises a taste masking effective amount of an artificial sweetener and at least one flavoring agent.

Preferably the flavoring agent is selected from the group consisting of natural flavors, natural fruit flavors, artificial flavors, artificial fruit flavors, peppermint, peppermint oils and mixtures thereof. For example only, without limiting the flavor to be incorporated into the formulation, the flavoring agent may be selected from cherry, grape, strawberry, orange-blood, melon, banana and citrus vanilla.

In one embodiment, the composition comprises more than one flavoring agent.

Preferably the sweetener is sucralose. More preferably sucralose is present in an amount of from about 5 grams to about 30 grams per liter of the composition.

In another embodiment the formulation further comprises glycerin. Preferably the amount of glycerin is from about 100 to about 900 grams per liter of the composition.

In yet another embodiment, the formulation further comprises hydroxyethylcellulose. Preferably the amount of hydroxyethylcellulose is from about 0.5 to about 3 grams per liter of the composition.

Preferably said liquid pharmaceutical formulation has a pH from about 2.5 to about 5.

In one embodiment, deferiprone is present at about 20 to about 200 grams per liter of the composition.

In another embodiment the formulation further comprises concentrated hydrochloric acid to preferably adjust the pH thereof and preferably in the range of 2.5 to 5.0.

The sweetening agent may be selected from the group consisting of a high intensity artificial sweetener such as aspartame, sucralose, sacharin or the like.

Preferably said sweetening agent is present at about 0.1 to about 3 percent by weight.

Most preferably deferiprone is present in an amount of about 50 to 200 grams per liter of the composition.

According to yet another aspect of the invention there is provided a palatable liquid pharmaceutical formulation comprising: about 50-200 grams of deferiprone per liter of the formulation, about 15 grams of sucralose per liter of the formulation, about 500 grams of glycerin per liter of the formulation, about 1 gram of hydroxyethylcellulose per liter of the formulation, about 59 grams of concentrated hydrochloric acid per liter of the formulation, about 0.40 grams of FD&C Yellow No. 6 per liter of the formulation, about 2 grams of artificial cherry flavour per liter of the formulation, about 0.10 grams of peppermint oil per liter of the formulation and a sufficient amount of purified water to yield 1 liter of the formulation.

In another embodiment said formulations may be used in iron overload conditions of the heart, the mitrochondria or the central nervous system including the brain.

DETAILED DESCRIPTION OF THE INVENTION

Artificial sweeteners that may be used in the present invention include, and are not limited to, aspartame, saccharin, saccharin sodium, sucralose or mixtures thereof. The taste masking effective amount of an artificial sweetener is that amount whereby the bitter taste of deferiprone is masked and the liquid pharmaceutical formulation is palatable.

Aspartame is used as a table-top sweetener and in beverage and food products and pharmaceutical and vitamin preparations to enhance flavor systems and to mask some unpleasant taste characteristics. Comparatively, aspartame has approximately 180-200 times the sweetening power of sucrose. The taste masking effective amount of aspartame has a range of from about 0.01 to about 40 grams per 100 mL.

Saccharin is used to enhance flavor systems and to mask some unpleasant taste characteristics and has approximately 500 times the sweetening power of sucrose. The taste masking effective amount of saccharin has a range of from about 0.1 to about 1 gram per 100 mL.

Saccharin sodium is considerably more soluble in water than saccharin, is used more frequently in pharmaceutical formulations and has approximately 300 times the sweetening power of sucrose. The taste masking effective amount of saccharin sodium has a range of from about 0.06 to about 5 grams per 100 mL.

Sucralose is characterized as an intensely sweet, trichlorinated carbohydrate, structurally similar to sucrose, having approximately 600 times the sweetening power of sucrose.

Mixtures of artificial sweeteners, such as a ratio of 10 parts to 1 part, have also been found to have synergistic sweetening properties and improve taste characteristics for some products.

A preferred embodiment of the taste masking formulation comprises a taste masking effective amount of the artificial sweetener sucralose. The amount of sucralose used masks the bitter taste of deferiprone.

Preferably, the taste masking effective amount of sucralose has a range of from about 0.05 to about 2.5 grams per 100 mL. More preferably, the taste masking effective amount of sucralose has a range of from about 0.5 to about 3 grams per 100 mL. Even more preferably, the taste masking effective amount of sucralose is about 1 gram per 100 mL.

The flavoring agent used is of the type and amount desired to enhance the palatability of the particular liquid pharmaceutical formulation to the intended consumer. Flavoring agents that may be used in the present invention include, and are not limited to, natural flavors, natural fruit flavors, artificial flavors, artificial fruit flavors, flavor enhancers or mixtures thereof. Natural flavors, artificial flavors or mixtures thereof include, and are not limited to, mint (such as peppermint or spearmint), and menthol. Natural fruit flavors, artificial fruit flavors or mixtures thereof include, but are not limited to, cherry. For example only, without limiting the flavor to be incorporated into the formulation, the flavoring agent may be selected from cherry, grape, strawberry, orange-blood, melon, banana and citrus vanilla. Although flavoring agents are generally provided as a minor component of the taste masking composition in amounts effective to provide a palatable flavor to the liquid pharmaceutical formulation, the addition of at least one flavoring agent is preferred, and more preferably, more than one flavoring agents may be employed.

Another embodiment of the taste masking composition further comprises a taste masking effective amount of an artificial sweetener, at least one flavoring agent, an optional sweetening agent and an optional debittering agent or mixtures thereof.

A pH stabilizer such as hydrochloric acid may be optionally added to the taste masked liquid pharmaceutical composition of the present invention to stabilize pH and prevent microbial growth. Hydrochloric acid is advantageously added since a lower pH will prevent microbial growth and add to the stability of the product.

Coloring agents also may be incorporated to provide an appealing color to the taste masked liquid pharmaceutical formulation. Suitable coloring agents are well known to those skilled in the art and are those that are deemed safe for human consumption by relevant governmental regulatory bodies and which avoid chemical incompatibilities with other ingredients.

In order to further illustrate the present invention and the advantages thereof, the following specific examples are given with the understanding that these examples are intended only to be illustrations without serving as a limitation on the scope of the present invention.

Formulation Development Rationale of Choice of Formulation

A deferiprone oral solution was developed to facilitate the administration of the active ingredient to patients with systemic iron overload, such as those with transfusion-dependent thalassemia or those with other disorders who may require an oral iron chelator, such as certain neurodegenerative diseases, who also have difficulty swallowing tablets, particularly when several tablets at a time are required.

Deferiprone oral solution was first developed for a phase I, open label, single-dose, three-way crossover relative bioavailability study of deferiprone tablets as compared to deferiprone solution under fasting and fed conditions in 15 healthy subjects. In the study the bioavailability of three 500 mg tablets of deferiprone was compared with that of a 1500 mg dose of deferiprone oral solution.

The initial developmental formulation of deferiprone oral solution contained deferiprone, hydrochloric acid, glycerin, saccharin sodium, peppermint oil, bitter blocker type flavour and purified water. Hydroxyethyl cellulose (Type H) was then added to this formulation to increase viscosity allowing for ease of dispensing. This formulation was used in the study.

Subsequently, the saccharin sodium and bitter blocker type flavour used in the oral solution formulation were replaced with sucralose and artificial cherry flavour. This helped improve the product taste. A colouring agent, FD & C Yellow No. 6 was added to the final formulation to improve the appearance of the product. The level of glycerol was decreased slightly. The modified formulation was used to manufacture the clinical batch for the study which was a phase I, randomized, open label, comparative, two-way crossover bioavailability study of deferiprone oral solution and deferiprone tablets under fasting conditions in 42 healthy subjects. The modified formulation was also used to manufacture the stability batches and is proposed for future commercial production.

TABLE 1

Comparative description of deferiprone oral solution formulations

| Ingredient and quality standard | Composition (g/L) | | |
|---|---|---|---|
| | F1 (Initial developmental formulation) | F2 | F3 (proposed for commercial production) |
| Deferiprone | 100.00 | 100.00 | 100.00 |
| Hydrochloric acid NF/EP | 50.0 | 50.0 | 59.0 |
| Glycerin EP | 250.00 | 600.00 | 500.00 |
| Hydroxyethyl cellulose Type H | Not used | 1.00 | 1.00 |
| Saccharin Sodium USP | 3.00 | 3.00 | Not used |
| Peppermint Oil | 0.100 | 0.10 | 0.10 |
| Bitter Blocker Type Flavour | 2.00 | 2.00 | Not used |
| Sucralose NF | Not used | Not used | 15.0 |
| Artificial cherry flavour | Not used | Not used | 2.00 |
| FD&C Yellow No. 6 | Not used | Not used | 0.40 |
| Purified Water USP | q.s. to batch size | q.s. to batch size | q.s. to batch size |

A phase I, randomized, open label, comparative, two-way crossover bioavailability study of deferiprone oral solution and Ferriprox® (deferiprone) tablets under fasting conditions was undertaken with the following results. The to-be-marketed formulation was used to manufacture the clinical batch for study. Deferiprone oral solution and Ferriprox® (deferiprone) tablets were tested in the study to determine the bioequivalency of the oral solution to the tablets in healthy subjects under fasting conditions. The two formulations were found to be bioequivalent.

In preparing a palatable formulation, it was determined that such could only be achieved via empiric study. Therefore a series of studies were conducted, which led to the establishment of a preferred formulation for treating patients with thalassemia. The most salient of these studies is described below. Subsequently, a formulation using a lower concentration and a different colour was developed to treat patients with iron-related neurodegenerative diseases, which is also considered to be part of the invention described herein.

To determine a formulation that could be used clinically, a series of experiments were conducted using an array of sweeteners and substances that mask the taste of a bitter deferiprone oral solution.

Taste Testing:

To decide the most suitable taste and flavor, a series of experiments were conducted with a group of 7 volunteers who were blinded as to the composition of different formulations.

Exercise #1

Six different formulations of Deferiprone oral solution were prepared using different artificial flavors; 1. cherry, 2. Lemon-lime, 3. Grape, 4. strawberry, 5. orange-blood and 6. citrus-vanilla while keeping all other exipients substantially the same as the original formulation presented.

1. The samples were randomized and assigned a sample number of 1-6.
2. Separate plastic spoons were used for each of the samples.
3. A randomized and individualized list of sample testing was supplied.
4. A score sheet for flavor and taste tolerability ranking was supplied.

5. Water was provided for rinsing after each test and the washing spit out into a container.
6. Participants tasted and swallowed a sample of each formulation as per individualized lists.
7. The testing sequence was different for each subject to minimize the influence of order on the results.
8. After each taste, participants rated the product of their choice using a 1-10 scale, 1 being the least acceptable value and 10, the most acceptable.

Exercise #2:

Cherry was the flavor of choice. However, there was a need for further improvement of the palatability of the formulation. A different concentration of sweetener was used and another set of five formulation were prepared, keeping all excipients the same except for different concentrations of sweeteners as listed below:

Formulation #1 Saccharin Sodium 6 g/L
Formulation #2 Saccharin Sodium 6 g/L+NaCl (0.9%)
Formulation #3 Saccharin Sodium 0.5 g/L+Acesulfame K 4.70 g/L
Formulation #4 Saccharin Sodium 1.5 g/L+D-Fructose 180.6 g/L
Formulation #5 Saccharin Sodium 3 g/L The preferred formulation was the one with 6 g/L concentration of Saccharin, but additional changes were desired as the taste had not been optimized.

Exercise #3

The sweetener was changed to Aspartame. After another round of taste testing the formulation with 10 g/L of Aspartame became the most acceptable formulation in terms of taste tolerability, but Aspartame is unstable at pH below 3.4 and this was confirmed by testing the degradation of Aspartame following 2 months storage.

Exercise #4

Now that Saccharin and Aspartame became unsuitable, a different sweetener "Xylitol", was used to prepare another set of four formulations (again keeping all other excipient the same) as listed below:

Formulation #1 Xylitol 30%
Formulation #2 Xylitol 40%
Formulation #3 Xylitol 20%+Saccharin Sodium 0.3%
Formulation #4 Xylitol 30%+Saccharin Sodium 0.3%

The participants concluded that the taste of the formulations with Xylitol was unacceptable. Xylitol even suppressed the Cherry flavor of the formulation.

Exercise #5

Sucralose was used as a 2% solution of Sucralose in 100 mg/ml of Deferiprone.

A set of 3 formulations with 0.5%, 1.0% and 2.0% of Sucralose concentrations were prepared. The formulation with 2% sucralose was preferred.

Further studies were conducted with Aspartame using a set of formulations at 0.5%, 1.0%, 1.3%, 1.5% and 1.7% concentration of Aspartame.

In order to make the taste testing results less influenced by the previous formulation, participants were given crackers to chew in between the tests, to neutralize any aftertaste that may influence the taste of other formulations. Again, in order to avoid any interference from the reaction, comments or body language from other participants, testing was conducted separately.

The taste of our solution was much more tolerable than the Pfertec product, a liquid formulation of deferiprone used as an unacceptable reference for comparison. The following charts provide the details of the product development.

Pharmaceutical Development

NAME: Deferiprone Oral Solution (US/Can)   LOT NO:
STRENGTH:   BATCH SIZE:   PRODUCT CODE:
100 mg/mL   1 L

| ITEM | MATERIAL NO. | QTY/L |
|---|---|---|
| Deferiprone |  | 100.00 g |
| Glycerin USP | 35158 | 600.00 g |
| Hydrochloric Acid NF/EP | 35162 | 50 mL |
| Hydroxyethyl Cellulose NF Type H | 35163 | 1.00 g |
| Saccharin Sodium USP | 35292 | 3.00 g |
| Peppermint Oil | 35264 | 0.10 g |
| Bitter Blocker type Flavour | 207184 | 2.00 g |
| Artificial Cherry Flavour | 35009 | 2.00 g |
| Purified Water USP/EP | 35244 | q.s to 1 L |

Pharmaceutical Development
Bulk Formulation Procedure

NAME: Deferiprone Oral Solution (EU)   LOT NO:
STRENGTH:   BATCH SIZE:   PRODUCT CODE:
100 mg/mL   1 L   1863 (EU)
PACKAGE:   EXPT. NO: f3 (12-F2)
DESCRIPTION: A clear slight yellow solution with peppermint and cherry-flavoured aroma

| ITEM | MATERIAL NO. | QTY/L | QTY/ BATCH |
|---|---|---|---|
| Deferiprone |  | 100.00 g | 100.00 g |
| Glycerin USP | 35158 | 500.00 g | 500.00 g |
| Hydrochloric Acid NF/EP | 35162 | 50 mL | 50 mL |
| Hydroxyethyl Cellulose NF Type H | 35163 | 1.00 g | 1.00 g |
| Sucralose NF | 226796 | 15.00 g | 15.00 g |
| Art. Cherry Flavour | 35009 | 2.00 g | 2.00 g |
| Peppermint Oil | 35264 | 0.10 g | 0.10 g |
| Purified Water USP/EP | 35244 | q.s to 1 L | q.s to 1 L |

Deferiprone Oral Solution Contains the Following Excipients:

Hydroxyethyl Cellulose Type HX EP

This excipient has a dual function in the formulation of deferiprone oral solution, acting as a thickener and as a suspension aid. It is used in oral and topical drug products as an inert ingredient. It is incorporated at 0.1% w/v in this formulation. It dissolves readily in water to give a clear, smooth, non-thixotropic solution. It has excellent compatibility with a large number of ingredients.

Glycerol EP

This excipient performs a dual function in the formulation of deferiprone oral solution, acting as a humectant and as a sweetening agent. As a humectant, glycerol promotes the retention of moisture. As a sweetening agent, it imparts a pleasant flavor in combination with sucralose NF, cherry flavour and peppermint oil. In liquid pharmaceutical formulations, glycerol is added at concentrations above 20% to serve as a preservative agent. In this formulation, it is incorporated at 50% w/v, which adds texture to the product making it easier for the patient to swallow.

Sucralose NF

This excipient acts as a sweetening agent. It is incorporated at 1.5% w/v in this formulation. Sucralose is widely used in the food industry as a non-nutritive, high intensity sweetener about 600 times sweeter than sugar. Sucralose does not break down in the human body; it is non-caloric and does not promote tooth decay.

Artificial Cherry Flavour

This excipient acts as a flavouring agent; it is incorporated in the formulation at 0.2% w/v. Its presence is to increase palatability of the oral solution.

Hydrochloric Acid NF/EP

This excipient acts as an acidifying agent; it is incorporated in the formulation at 5.9% w/v.

Peppermint Oil

This excipient acts as a flavouring agent; it is incorporated in the formulation at 0.01% w/v. Its presence is to increase palatability of the oral solution.

FD & C Yellow No. 6

This excipient acts as a colouring agent; it is incorporated in the formulation at 0.04% w/v.

Bulk Formulation Procedure

| ITEM | MATERIAL NO. | QTY/L | QTY/ BATCH |
|---|---|---|---|
| Deferiprone | | 100.00 g | 100.00 g |
| Glycerin USP | 35158 | 500.00 g | 500.00 g |
| Hydrochloric Acid NF/EP | 35162 | 50 mL | 50 mL |
| Hydroxyethyl Cellulose NF Type H | 35163 | 1.00 g | 1.00 g |
| Sucralose NF | 226796 | 15.00 g | 15.00 g |
| Art. Cherry Flavour | 35009 | 2.00 g | 2.00 g |
| Peppermint Oil | 35264 | 0.10 g | 0.10 g |
| FD & C Yellow No. 6 (#10-21-DA-4415) | 35285 | 0.4 g | 0.4 g |
| Purified Water USP/EP | 35244 | q.s to 1 L | q.s to 1 L |

Pharmaceutical Development
Bulk Formulation Procedure
Procedure:
1. In a suitable container take about 30% batch size of Purified Water USP/EP. Start heating and mixing using a propeller mixer until a vortex is formed. While heating and mixing, add slowly Hydroxyethyl Cellulose NF Type H into the container and mix until dissolved (20 min.).
Speed Reading 588 rpm
2. Cool down the above to room temperature. While mixing, add Glycerin USP into the above container and mix until uniform solution is obtained (5 min.).
Speed Reading 653 rpm
3. While mixing add Deferiprone into above and mix until uniform dispersion is obtained (10 min.).
Speed Reading 653 rpm
4. While mixing add Hydrochloric Acid NF/EP into above and mix until a clear solution is obtained (10 min.).
Speed Reading 653 m
5. While mixing add Sucralose NF/EP into above and mix until dissolved (12 min.).
Speed Reading 653 rpm
6. While mixing add Peppermint Oil and Art. Cherry Flavour into above and mix (10 min.).
Speed Reading 653 rpm
7. Dissolve F D & C Yellow No. 6 (#10-21-DA-4415) in 2% batch size of Purified Water USP/EP, and mix using magnetic stirrer.
8. While mixing the solution of step 6, add dye solution from step 7 to step 6.
9. Bring the volume of step 8 solution to the final batch size using Purified Water USP/EP. Mix thoroughly (5 min.).
Speed Reading 653 rpm
10. Check pH of the final bulk (Range 2.8-3.0)

A preservative may or may not be included with the formulation. In the example that follows methylparaben NF and Propylparaben NF were used to evaluate the value of a preservative in the final formulation. Other appropriate preservatives may be used as well provided they are selected giving due consideration to the impact on the other qualities of the formulation.

Preparation of Preservatives Stock Solution:

Dispense 23.9 g of Purified water USP/EP in a pre-tare suitable container and heat it to 80° C.-90° C. and add 1.00 g of Methylparaben NF and 0.10 g of Propylparaben NF. Mix thoroughly until dissolved. Use this stock solution in step #8 as follows: Note: The weight of stock solution should be 25.0 g.

| Part# | Qty of stock solution to be added | % of Label Claim | Methyl-paraben NF | Propyl-paraben NF |
|---|---|---|---|---|
| 1 | 1.0 g | 20% | 0.04 g | 0.004 g |
| 2 | 2.0 g | 40% | 0.08 g | 0.008 g |
| 3 | 3.0 g | 60% | 0.12 g | 0.012 g |
| 4 | 4.0 g | 80% | 0.16 g | 0.016 g |
| 5 | 5.0 g | 100% | 0.2 g | 0.02 g |

Procedure:
1. In a suitable container take about 30% batch size of Purified Water USP/EP and start heating 80° C.-90° C. and mixing using a propeller mixer. While continuing mixing and marinating the temperature add slowly Hydroxyethyl Cellulose NF Type H and mix until dissolved.
2. Cool down the above solution to room temperature.
While mixing, add Glycerin USP into the above container and mix until uniform solution is obtained.
3. While mixing add Deferiprone into above and mix until uniform dispersion is obtained.
4. While mixing add Hydrochloric Acid NF/EP into above and mix until a clear solution is obtained.
5. While mixing add Sucralose NF/EP into above and mix until dissolved.
6. While mixing add Peppermint Oil and Art. Cherry Flavour into above and mix until uniform.
7. Dissolve F D & C Yellow No. 6(#10-21-DA-4415) in 2% batch size of Purified Water USP/EP, and mix using magnetic stirrer.
8. Divide the above bulk into 5 equal parts by weight. To each part add the proposed quantity of stock solution (see above for quantity of stock solution to be added) to get the label claims of preservatives. Record as specified.
9. Bring the volume of each part from above step to 200 mL with Purified water USP/EP. Mix each part thoroughly until uniform.
10. Check pH of the final bulk (Range 2.8-3.0)

The tolerability, safety and efficacy of our liquid formulation of deferiprone were assessed in a multi-national, open label study in 100 iron-overloaded pediatric patients (≤10 years of age) with transfusion-dependent anemias. Deferiprone was given in a special formulation to mask the taste, similar to that described, using a concentration of 100 mg/ml at a total daily dose of 50 mg/kg, divided in 3 doses, for the first 2 weeks and then increased to a total daily dose of 75 mg/kg or 100 mg/kg/day if required. The oral solution was tolerated well by all children and there were no unexpected adverse reaction. In fact, the data suggest that there was lower incidence of gastrointestinal adverse reactions (vomiting; 6% of patients; abdominal pain=3% and no reports of nausea) than what has been reported with the tablet formulation of deferiprone (nausea=16% of patients; vomiting=13%; abdominal pain=14%) in previous studies.

As many changes can be made to the preferred embodiment of the invention without departing from the scope thereof. It is considered that all matter contained herein be considered as illustrative of the invention but not in a limiting sense.

What is claimed is:

1. An oral pharmaceutical liquid formulation comprising deferiprone in a concentration of from about 20 grams to about 200 grams per liter of liquid formulation and a taste masking composition, said taste masking composition comprising:
   a sweetener selected from the group consisting of aspartame, saccharin, saccharin sodium, sucralose and mixtures thereof, in a concentration of about 0.1 grams to about 400 grams per liter of liquid formulation;
   hydroxyethylcellulose as a thickening and suspension aid, in a concentration of from about 0.5 grams to about 3.0 grams per liter of liquid formulation;
   glycerin as a humectant in an amount of about 100 grams to about 900 grams per liter of liquid formulation; and
   at least one flavoring agent selected from the group consisting of natural flavors, natural fruit flavors, artificial flavors, artificial fruit flavors, peppermint, peppermint oils and mixtures thereof;
   wherein the remainder of the liquid formulation is purified water.

2. The formulation of claim 1 further comprising more than one flavoring agent.

3. The formulation of claim 1, wherein the sweetener is sucralose.

4. The formulation of claim 1, wherein said liquid pharmaceutical formulation has a pH from about 2.5 to about 5.0.

5. The formulation of claim 1, wherein the amount of glycerin is about 500 grams per liter of the formulation.

6. The formulation of claim 1, wherein the amount of hydroxyethylcellulose is about 1.0 grams per liter of the formulation.

7. The formulation of claim 4, further comprising concentrated hydrochloric acid.

8. The formulation of claim 1, wherein the sweetening agent is selected from the group consisting of an artificial sweetener selected from the group consisting of aspartame, sucralose and saccharin.

9. The formulation of claim 1, wherein said sweetening agent is present at about 0.1 to about 3 percent by weight of the formulation.

10. The formulation of claim 1, wherein deferiprone is present in an amount of about 50 grams to about 200 grams per liter of the formulation.

11. The formulation of claim 1 wherein the flavoring agent further comprises artificial cherry flavor.

12. The formulation of claim 11 wherein peppermint oil is added as an additional flavor.

13. A liquid pharmaceutical formulation comprising: about 50 to about 200 grams of deferiprone per liter of the formulation, about 15 grams of sucralose per liter of the formulation, about 500 grams of glycerin per liter of the formulation, about 1 gram of hydroxyethylcellulose per liter of the formulation, about 59 grams of concentrated hydrochloric acid per liter of the formulation, about 0.40 grams of FD&C Yellow No. 6 per liter of the formulation, about 2 grams of artificial cherry flavour per liter of the formulation, about 0.10 grams of peppermint oil per liter of the formulation and a sufficient amount of purified water to yield 1 liter of the formulation.

14. The formulation of claim 1, wherein the flavoring agent is selected from the group consisting of cherry, grape, strawberry, orange-blood, melon, banana, and citrus vanilla, and mixtures thereof.

15. The formulation of claim 1, wherein the sweetener is present in an amount of from about 5 grams to about 30 grams per liter of the formulation.

16. The formulation of claim 15, wherein the sweetener is sucralose.

17. A method of treating a patient with iron overloading in a heart, a mitochondria, or a central nervous system including brain, comprising administering to the patient orally the liquid formulation of claim 1.

* * * * *